(12) United States Patent
Tang

(10) Patent No.: US 9,999,754 B2
(45) Date of Patent: Jun. 19, 2018

(54) DELIVERY METHOD FOR BIODEGRADABLE STENTS

(71) Applicant: Gyrus ACMI, Inc., Southborough, MA (US)

(72) Inventor: Hui Tang, Acton, MA (US)

(73) Assignee: Gyrus ACMI, Inc., Southborough, MA (US)

( * ) Notice: Subject to any disclaimer, the term of this patent is extended or adjusted under 35 U.S.C. 154(b) by 149 days.

(21) Appl. No.: 14/948,421

(22) Filed: Nov. 23, 2015

(65) Prior Publication Data

US 2016/0157987 A1    Jun. 9, 2016

Related U.S. Application Data

(60) Provisional application No. 62/089,300, filed on Dec. 9, 2014.

(51) Int. Cl.
*A61F 2/04* (2013.01)
*A61M 27/00* (2006.01)
*A61M 25/09* (2006.01)

(52) U.S. Cl.
CPC ... *A61M 27/008* (2013.01); *A61F 2210/0004* (2013.01); *A61M 2025/09133* (2013.01)

(58) Field of Classification Search
CPC .................................................... A61M 25/00
USPC .............................................. 623/1.11–1.25
See application file for complete search history.

(56) References Cited

U.S. PATENT DOCUMENTS

| | | | |
|---|---|---|---|
| 5,401,257 A * | 3/1995 | Chevalier, Jr. .... | A61M 25/0017 604/265 |
| 5,437,288 A * | 8/1995 | Schwartz .............. | A61M 25/09 600/434 |
| 8,246,691 B2 | 8/2012 | Mangiardi | |
| 8,696,728 B2 | 4/2014 | Hebert | |
| 2007/0005024 A1* | 1/2007 | Weber .................... | A61L 29/14 604/265 |
| 2009/0297635 A1* | 12/2009 | Sheth ................... | A61L 31/041 424/722 |
| 2011/0098803 A1 | 4/2011 | Gale | |
| 2011/0190864 A1 | 8/2011 | McClain | |
| 2012/0171260 A1 | 7/2012 | Huang | |
| 2012/0296407 A1 | 11/2012 | Caselnova | |
| 2013/0310912 A1 | 11/2013 | Breitenkamp | |
| 2014/0188243 A1 | 7/2014 | Zheng | |

FOREIGN PATENT DOCUMENTS

| | | |
|---|---|---|
| WO | 2004112863 A1 | 12/2004 |
| WO | 2010033943 A1 | 3/2010 |
| WO | 2011097103 A1 | 8/2011 |

* cited by examiner

*Primary Examiner* — Yashita Sharma
(74) *Attorney, Agent, or Firm* — Gerald P. Kazanjian; Yi Chen

(57) ABSTRACT

Provided are methods, systems, and kits of properly delivering a biodegradable stent into a body lumen of a subject. More particularly, provided are methods, systems, and kits of properly delivering a biodegradable ureteral stent into the kidney and the bladder of a subject. Even more particularly, provided are methods, systems, and kits of properly delivering a chitosan based stent into a body lumen of a subject. Even more particularly, provided are methods, systems, and kits of properly delivering a chitosan based ureteral stent into the kidney and the bladder of a subject.

4 Claims, 9 Drawing Sheets

Guild Wire (GW) Compatibility with 6 Fr. PASTA Stent

| Guild Wires (GWs) | Benchmark (n= 6) | Pre-hydration (n= 6) | New ID (n= 3) |
|---|---|---|---|
| REF 15 E-Z GLIDER GW (0.025") | Good | Good | N/A |
| REF 35 E-Z GLIDER GW (0.035") | N/A | N/A | Good |
| REF 38 E-Z GLIDER GW (0.038") | N/A | N/A | Good |
| REF 23 PTFE Coated GW (0.025") | Poor | Poor | N/A |
| REF 24 PTFE Coated GW (0.038") | N/A | N/A | No |
| REF 25 PTFE Coated GW (0.035") | No | No | N/A |
| REF 26 PTFE Coated GW (0.038") | N/A | N/A | No |
| REF 28 PTFE Coated GW (0.038") | No | No | N/A |

Note: PTFE coated GW has compatibility issue with 6 Fr. PASTA stent at both benchmark and pre-hydration.

Figure 9

DELIVERY METHOD FOR BIODEGRADABLE STENTS

CROSS-REFERENCE TO RELATED PATENTS

This application claims the benefit of priority to U.S. Provisional Patent Application No. 62/089,300 filed on Dec. 9, 2014. The entire teachings of the above application are incorporated herein by reference.

FIELD

The embodiments of the present invention relate generally to methods, systems and kits of delivering biodegradable stents to a treatment site of a subject. More particularly, the embodiments of the present invention relate to methods, systems and kits of delivering chitosan based biodegradable stents to a treatment site of a subject.

BACKGROUND

Chitin and Chitosan derivatives are a family of biopolymers containing N-acetyl-D-glucosamine and D-glucosamine subunits. Chitin is widely found in the exoskeletons of arthropods, shells of crustaceans, and the cuticles of insects while chitosan is mostly produced in industry by alkaline hydrolysis of chitin. Both chitin and chitosan are promising polymers for a variety of applications. The biomedical applications of chitin and chitosan are of particular interest because of their biocompatibility, biodegradability and structural similarity to the glycosaminoglycans. Their medical and biomedical applications and potential applications include dressings for wound-healing, tissue engineering applications, artificial kidney membranes, drug delivery systems, absorbable sutures, hemostats, antimicrobial applications, as well as applications in dentistry, orthopedics, ophthalmology, and plastic surgery. Despite these potential applications of chitin and chitosan, few chitin or chitosan products are practically in commercial use. Actually, there appears to be no commercially available chitosan based stents currently on the market even though there are reports of chitosan based stents, for example, as disclosed in U.S. Pat. No. 8,414,925.

In the process of developing chitosan based biodegradable stents, it's surprisingly found that using the conventional polytetrafluoroethylene (PTFE) coated guidewires to deliver these chitosan based stents into a body lumen of a subject is extremely difficult, or impossible due to the fact that these chitosan based stents would buckle, re-coil, or not be in a proper position during the delivering process. As a result, there is a practical need for methods and systems for properly delivering these chitosan based stents into a body lumen of a subject in order to utilize the benefits and advantages of the chitosan and chitin based products as indicated in previous paragraph.

BRIEF SUMMARY

One object of the present invention is to provide a method of properly deploying a biodegradable stent into a treatment site of a subject. Another object of the present invention is to provide a method of properly deploying a chitosan based biodegradable stent into a treatment site of a subject. Yet another object of the present invention is to provide a method of properly deploying a biodegradable ureteral stent into a treatment site of a subject. Still yet another object of the present invention is to provide a method of properly deploying a biodegradable ureteral stent into the ureter of a subject to allow urine drainage, and/or pressure relief, and/or removal of kidney stones, and/or treatment of ureter obstructions or impairments. Yet another object of the present invention is to provide a method of properly deploying a chitosan based ureteral stent into a ureter of a subject to allow urine drainage, and/or pressure relief, and/or removal of kidney stones, and/or treatment of ureter obstructions or impairments.

The embodiments of the present invention relate generally to methods, systems, and kits for deploying biodegradable stents into a treatment site of a subject. More particularly, the embodiments of the present invention relate to methods, systems, and kits for deploying a biodegradable ureteral stent into a treatment site of a patient. Even more particularly, the embodiments of the present invention relate to methods, systems, and kits for deploying a biodegradable chitosan based ureteral stent into the ureter of a subject for the purpose of urinary drainage from the kidney to the bladder, and/or for pressure relief, and/or for removal of kidney stones, and/or for the treatment of ureter obstructions or impairments In one embodiment, the present invention provides a method of identifying a guidewire for a proper delivery of a biodegradable stent into a treatment site of a subject, the method comprising determining the surface hydrophilicity or surface hydrophobicity of the guidewire; and determining the surface hydrophilicity or surface hydrophobicity of the biodegradable stent, wherein the guidewire is likely proper for the delivery of the stent into the treatment site of the subject when the guidewire and the stent both have a hydrophilic surface or both have a hydrophobic surface.

In one embodiment, the present invention provides a method of identifying a guidewire for a proper delivery of a biodegradable ureteral stent into a treatment site of a subject; the method comprising determining the surface hydrophilicity or surface hydrophobicity of the guidewire; and determining the surface hydrophilicity or surface hydrophobicity of the ureteral stent, wherein the guidewire is likely proper for the delivery of the ureteral stent into the treatment site of the subject when the guidewire and the ureteral stent both have a hydrophilic surface or both have a hydrophobic surface.

In one embodiment, the present invention provides a method of identifying a guidewire for a proper delivery of a chitosan based stent into a treatment site of a subject; the method comprising determining the surface hydrophilicity or surface hydrophobicity of the guidewire; and determining the surface hydrophilicity or surface hydrophobicity of the chitosan based stent, wherein the guidewire is likely proper for the delivery of the chitosan based stent into the treatment site of the subject when the guidewire and the chitosan based stent both have a hydrophilic surface or both have a hydrophobic surface.

In one embodiment, the present invention provides a method of identifying a guidewire for a proper delivery of a chitosan based ureteral stent into the ureter of a subject for the purpose of urinary drainage from the kidney to the bladder, and/or pressure relief, and/or removal of kidney stones, and/or treatment of ureter obstructions and impairments; the method comprising determining the surface hydrophilicity or surface hydrophobicity of the guidewire; and determining the surface hydrophilicity or surface hydrophobicity of the chitosan based ureteral stent, wherein the guidewire is likely proper for the delivery of the chitosan based ureteral stent into the ureter of a subject when the guidewire and the chitosan based ureteral stent both have a hydrophilic surface or both have a hydrophobic surface.

In one embodiment, the present invention provides a method of properly delivering a biodegradable stent into a treatment site of a subject, the method comprising determining the surface hydrophilicity or surface hydrophobicity of a guidewire; determining the surface hydrophilicity or surface hydrophobicity of a biodegradable stent, wherein the guidewire is likely proper for the delivery of the biodegradable stent into the treatment site of the subject when the guidewire and the biodegradable stent both have a hydrophilic surface or both have a hydrophobic surface; and inserting the biodegradable stent into the treatment site of the patient using the identified guidewire.

In one embodiment, the present invention provides a method of properly delivering a biodegradable ureteral stent into a treatment site of a subject, the method comprising determining the surface hydrophilicity or surface hydrophobicity of a guidewire; determining the surface hydrophilicity or surface hydrophobicity of a biodegradable ureteral stent, wherein the guidewire is likely proper for the delivery of the ureteral stent into the treatment site of the subject when the guidewire and the ureteral stent both have a hydrophilic surface or both have a hydrophobic surface; and inserting the biodegradable ureteral stent into the treatment site of the patient using the identified guidewire.

In one embodiment, the present invention provides a method of properly delivering a chitosan based stent into a treatment site of a subject, the method comprising determining the surface hydrophilicity or surface hydrophobicity of a guidewire; determining the surface hydrophilicity or surface hydrophobicity of a chitosan based stent, wherein the guidewire is likely proper for the delivery of the chitosan based stent into the treatment site of the subject when the guidewire and the chitosan based stent both have a hydrophilic surface or both have a hydrophobic surface; and inserting the chitosan based stent into the treatment site of the patient using the identified guidewire.

In one embodiment, the present invention provides a method of properly delivering a chitosan based ureteral stent into a subject's ureter, the method comprising determining the surface hydrophilicity or surface hydrophobicity of a guidewire; determining the surface hydrophilicity or surface hydrophobicity of a chitosan based ureteral stent, wherein the guidewire is likely proper for the delivery of the chitosan based ureteral stent into the ureter of a subject when the guidewire and the chitosan based ureteral stent both have a hydrophilic surface or both have a hydrophobic surface; and inserting the chitosan based stent into the ureter of the subject using the identified guidewire.

In one embodiment, the present invention provides a kit for a proper delivery of a biodegradable stent into a treatment site of a subject; the kit comprising a guidewire, a biodegradable stent, and instructions for measuring surface hydrophilicity or surface hydrophobicity of a guidewire and/or a biodegradable stent. The kit may further comprise instructions for using a guidewire and/or using a biodegradable stent.

In one embodiment, the present invention provides a kit for a proper delivery of a biodegradable ureteral stent into a treatment site of a subject, the kit comprising a guidewire, a biodegradable ureteral stent, and instructions for measuring surface hydrophilicity or surface hydrophobicity of a guidewire and/or a biodegradable ureteral stent. The kit may further comprise instructions for using a guidewire and/or using a biodegradable ureteral stent.

In one embodiment, the present invention provides a kit for a proper delivery of a chitosan based stent into a treatment site of a subject, the kit comprising a guidewire, a chitosan based stent, and instructions for measuring surface hydrophilicity or surface hydrophobicity of a guidewire and/or a chitosan based stent. The kit may further comprise instructions for using a guidewire and/or using a chitosan based stent.

In one embodiment, the present invention provides a kit for a proper delivery of a chitosan based ureteral stent into a subject's ureter for the purpose of urinary drainage from the kidney to the bladder, the kit comprising a guidewire, a biodegradable stent, and instructions for measuring surface hydrophilicity or surface hydrophobicity of a guidewire and/or a chitosan based ureteral stent. The kit may further comprise instructions for using a guidewire and/or using a chitosan based ureteral stent.

In one embodiment, the present invention provides a biodegradable stent delivery system for a proper delivery of a biodegradable stent into a treatment site of a subject, the system comprising a biodegradable stent, a guidewire, and accessories for measuring surface hydrophilicity or surface hydrophobicity of a guidewire and/or a biodegradable stent, and instructions for inserting a biodegradable stent into a treatment site of a subject when it is determined that the guidewire and the biodegradable stent both have a hydrophilic surface, or both have a hydrophobic surface.

In one embodiment, the present invention provides a biodegradable ureteral stent delivery system for a proper delivery of a biodegradable ureteral stent into a treatment site of a subject, the system comprising a biodegradable ureteral stent, a guidewire, and accessories for measuring surface hydrophilicity or surface hydrophobicity of a guidewire and/or a biodegradable ureteral stent, and instructions for inserting a biodegradable ureteral stent with a guidewire into a treatment site of a subject when it is determined that the guidewire and the biodegradable ureteral stent both a hydrophilic surface or both have a hydrophobic surface.

In one embodiment, the present invention provides a system for identifying a guidewire for the proper delivery of a chitosan based stent into a treatment site of a subject, the system comprising a chitosan based stent, a guidewire, and accessories for measuring surface hydrophilicity or surface hydrophobicity of a guidewire and/or a chitosan stent, and instructions for inserting a chitosan based stent with a guidewire into a treatment site of the subject when it is determined that the guidewire and the chitosan based stent both have a hydrophilic surface or both have a hydrophobic surface.

In yet another embodiment, the present invention provides a chitosan based ureteral stent delivery system for a proper delivery of a chitosan based ureteral stent into a subject's ureter for the purpose of urinary drainage from the kidney to the bladder, the system comprising a chitosan based ureteral stent, a guidewire, and accessories for measuring surface hydrophilicity or surface hydrophobicity of a guidewire and/or a chitosan based ureteral stent, and instructions for inserting a chitosan based ureteral stein with a guidewire into a treatment site of the subject when it is determined that the guidewire and the chitosan based ureteral stent both have a hydrophilic surface or both have a hydrophobic surface.

In some embodiments, the present invention also provides a method of treating urological or kidney related diseases with a biodegradable stent, the method comprising providing a proper guidewire in accordance with its surface hydrophilicity or surface hydrophobicity; and inserting the biodegradable stent into the treatment site of a subject using the provided guidewire, wherein the biodegradable stent optionally contains one or more therapeutic agents.

In some embodiments, the present invention also provides a method of treating urological or kidney related diseases with a biodegradable ureteral stent, the method comprising providing a proper guidewire in accordance with its surface hydrophilicity or surface hydrophobicity; and inserting the biodegradable ureteral stent into the treatment site of a subject using the provided guidewire, wherein the biodegradable ureteral stent optionally contains one or more therapeutic agents.

In some embodiments, the invention further provides a method of treating urological or kidney related diseases with a chitosan based stent, the method comprising providing a proper guidewire in accordance with its surface hydrophilicity or surface hydrophobicity; and inserting the chitosan based stent into the treatment site of a subject using the provided guidewire, wherein the chitosan based stent optionally contains one or more therapeutic agents.

In some embodiments, the invention further provides a method of treating urological or kidney related diseases with a chitosan based ureteral stent, the method comprising providing a proper guidewire in accordance with its surface hydrophilicity or surface hydrophobicity; and inserting the chitosan based ureteral stent into the treatment site of a subject using the provided guidewire, wherein the chitosan based ureteral stent optionally contains one or more therapeutic agents.

BRIEF DESCRIPTION OF THE FIGURES

FIG. 9 shows the compatibility profile of several guidewires with the chitosan based stents.

DETAILED DESCRIPTION

Definitions

Figure 1:
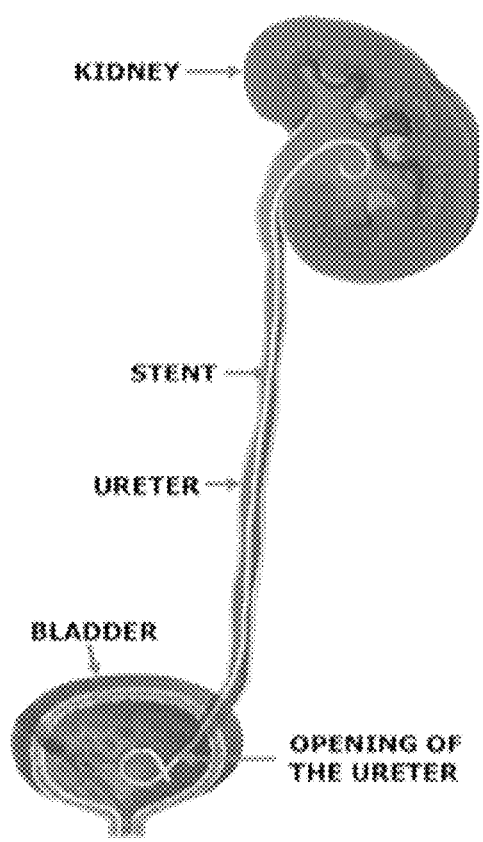
FIG. 1 is an illustrative picture showing a ureteral stent positioned between the kidney and the bladder of a subject.

Unless otherwise specified, the following terms and phrases shall have the meanings as set forth below:

The terms "one embodiment", "some embodiments", "other embodiments", and similar expressions indicate that the embodiment or embodiments described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it would be within the knowledge of one skilled in the art to incorporate such feature, structure, or characteristic into other embodiments, whether or not explicitly described, unless clearly stated to the contrary. That is, the various individual elements described below, even if not explicitly shown in a particular combination, are nevertheless contemplated as being combinable with each other to form other additional embodiments or to complement and/or enrich the described embodiment or embodiments, as would be understood by one of ordinary skill in the art.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to". The term "or" is used herein to mean, and is used interchangeably with, the term "and/or," unless context clearly indicates otherwise.

The term "such as" is used herein to mean, and is used interchangeably, with the phrase "such as but not limited to". Unless specifically stated or obvious from context, as used herein, the term "about" is understood as within a range of normal acceptance in the art, for example within standard deviations of the mean.

All numeric values are herein assumed to be modified by the term "about" whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. Even more specifically, "about" can be understood as within 10%, 9%, 8%, 7%, 6%, 5%, 4%, 3%, 2%, 1%, 0.5%, 0.1%, 0.05%, or 0.01% of the stated value.

As used herein, the term "subject" refers to human and non-human animals, including veterinary subjects. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human and may be referred to as a patient.

As used herein, the terms "treat," "treating" or "treatment" refers, preferably, to an action to obtain a beneficial or desired clinical result including, but not limited to, alleviation or amelioration of one or more signs or symptoms of a disease or condition, diminishing the extent of disease, stability (i.e., not worsening) state of disease, amelioration or palliation of the disease state, diminishing rate of or time to progression, and remission (whether partial or total), whether detectable or undetectable. "Treatment" can also mean prolonging survival as compared to expected survival in the absence of treatment. Treatment does not need to be curative.

Ranges provided herein are understood to be shorthand for all of the values within the range. For example, a range of 1 to 10 is understood to include any number, combination of numbers, or sub-ranges such as 1, 1.5, 2.0, 2.8, 3.90, 4, 5, 6, 7, 8, 9, and 10.

"Determining" as used herein is understood as performing an assay, an experiment, or using a diagnostic method to ascertain the state of someone or something, e.g., the presence, absence, level, or degree of a certain condition, biomarker, disease state, or physiological condition.

The term "biodegradable" as used herein is interchangeable with the terms "bioabsorbable" or "bioerodable", and generally refers to polymers that are capable of being completely degraded and/or eroded when exposed to bodily fluids such as blood and can be gradually resorbed, absorbed, and/or eliminated by the body. The processes of breaking down and absorption of the polymer in a stent can be caused by, for example, hydrolysis and metabolic processes.

In some aspects, the biodegradable polymers that are suited for a biodegradable stent, particularly a biodegradable ureteral stent, should exhibit at least some of the following characteristics: high tensile strength, high retention coil strength, excellent biocompatibility and biodurability, excellent radiopacity or flouroscopic visibility, availability in varying durometers, and a low resistance to passage.

"A biodegradable stent" is used herein to mean a stent made from biodegradable polymers. Representative examples of polymers that may be used for making a biodegradable stent include, but are not limited to, poly(N-acetylglucosamine) (chitin), chitosan, poly(hydroxyvalerate), poly(lactide-coglycolide), poly(hydroxybutyrate), poly(hydloxybutyrateco-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrilestyrene copolymers, ABS resins, polyamides (such as Nylon 66 and polycaprolactam), polycarbonates, polyoxymethylenes, polyimides, polyethers, polyurethanes, rayon, rayontriacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be suited for use in fabricating a biodegradable stent include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol. The properties and usages of these biodegradable polymers are known in the art, for example, as disclosed in U.S. Pat. No. 8,017,144 and U.S. application publication No. 2011/0,098,803.

In some aspects, a biodegradable stent as described herein may be made from polylactic acid (PLA), polyglycolic acid (PGA), poly(D,L-lactide-co-glycolide), polycaprolactone, or copolymers thereof.

In some aspects, a biodegradable stent as described herein may be made from polyhydroxy acids, polyalkanoates, polyanhydrides, polyphosphazenes, polyetheresters, polyesteramides, polyesters, and polyorthoesters.

In some preferable aspects, a biodegradable stent as described herein may be made from chitosan, collagen, elastin, gelatin, fibrin glue, or combinations thereof.

"Chitosan based stent", "chitosan stent" "chitosan based ureteral stent", and "chitosan ureteral stent" as described herein mean that the major component of a stent comes from chitosan. For example, a chitosan based stent as described herein may contain chitosan at least in an amount of over 50%, or over 60%, or over 70%, or over 80% weight percentage of the total stent weight. Even more particularly, a chitosan based stent as described herein may have the chitosan content in an amount of between about 70% and about 85% weight percentage of the total chitosan stent.

A chitosan based stent as described herein may also be coated with a polymer layer in order to adjust degradation times. For example, a chitosan based stent as described herein may be dip-coated with a solution of poly(D,L-lactide-co-glycolide) in acetone.

A chitosan based stent may also be coated with a layer of barium sulfate, by dipping the stents into an aqueous suspension of barium sulfate. In some aspects, the weight of the coated barium sulfate may be in an amount of between about 15 and between about 30 weight percentage of the total weight of the stent. Additionally, a chitosan stent may be perforated.

A ureteral stent as used herein may be used to aid in transfer of urine from one of the kidneys of a subject to the bladder where obstructions or other conditions may inhibit normal flow by creating a bypath around a blockage. It is typically placed within a cavity of a patient such that one portion of the ureteral stent is located in a kidney of the patient and another portion of the ureteral stent is located in a bladder of the patient. A typical ureteral stent is a 5-7 F tube/catheter, with an anchoring coil on either end, one positioned in the renal pelvis of the kidney, the other in the bladder such as disclosed in PCT application publication No. WO2014/116,718.

A chitosan based ureteral stent as described herein should be able to satisfy some mechanical requirements. First, it should be capable of withstanding the structural loads, namely radial compressive forces, imposed on the stent as it supports the walls of a ureter. Consequently, the chitosan stent should possess adequate radial strength. The chitosan based stent should adequately maintain its size and shape throughout its service life despite the various forcers that may come to bear on it, for example, a radially directed force may tend to cause a stent to recoil inward. Generally, it is desirable to minimize recoil of a stent. Moreover, a chitosan based stent should possess sufficient flexibility to allow for crimping, expansion. Longitudinal flexibility is important to allow a chitosan stent to conform to a deployment site that may not be linear.

The chitosan based ureteral stents as described herein may have some desirable biodegradation properties such that these stents provide maximum functional efficacy and patient comfort during implantation and avoid a second surgical treatment. In some aspects, these chitosan based ureteral stents can be removed from the patient's body in a highly controllable fashion, by adjusting the pH of the patient's urine, which can be done by treatment with basic or acidic compounds added to the diet. These methods of pH-adjustment of the urine are well-known in the clinical practice. For example, a basic pH may be maintained by giving a base or basic salt, such as acetazolamide or bicarbonate, to the patient for a desired period of time, e.g. 2 weeks, after which the urine may be made acidic (if not naturally back-regulated to an acidic pH) by giving an acid or acidic salt, such as ammonium chloride, which will, at a pH of less than about 6, result in a fast dissolution of the chitosan stent and its disappearance from the body. Moreover, a general feature of these chitosan based stents may further have inherent antibacterial potential, thereby making chitosan based stents highly promising for urological applications to prevent stent- or catheter-related infections.

In some preferable aspects, a chitosan based ureteral stent as described herein may achieve the best result when used for a subject in a urine pH range of between about 6 and about 8. Preferably, a chitosan based ureteral stent will be kept inside the ureter of a subject for about 2-8 weeks, more preferably, for about 2-6, weeks, or even more preferably for 2-4 weeks.

The biodegradable stents, chitosan based stents, chitin based stents, and chitosan based ureteral stents as described herein may be made in accordance with the material, procedures, and methods as disclosed in the art, for example, in U.S. Pat. No. 8,414,925, and U.S. application publication Nos. US 2011/0,098,803, US 2011/0,098,803, and US 2005/0,163,821.

A guidewire as used herein is an elongate member of sufficient stiffness such that it may be maneuvered within a bodily cavity of the patient to position the guidewire within the bodily cavity of the patient. It may be any conventional guidewire such as a Glidewire® guidewire, a Zebra® guidewire, a Lubriglide coated guidewire, a PTFE coated guidewire, or an E-Z Glider® guidewire. The materials and methods of making guidewires are well established in the art, and can be found, for example, in U.S. Pat. Nos. 6,436,056, and 4,538,622, and PCT application publication No. WO 2004/082,632.

In some aspects, hydrogel coated guidewires described herein are commercially available. In some aspects, some specific hydrogel coated guidewires can be made in accordance with known methods, for example, as disclosed in EP 1,740,234 B1 and U.S. application publication No. US 2005/0,214,492.

A typical ureteral guidewire may have a length of between about 130 cm and about 180 cm. More specifically, a ureteral guidewire may have a length of between about 140 cm and about 160 cm.

The terms "inserting a stent", "delivering a stent", "placing a stent", "employing a stent", and similar expressions as described herein all mean introducing and transporting a stent through a bodily lumen into a region that requires treatment by a guidewire. In general, it is done by positioning a stent on one end of the guidewire, inserting the end of the guidewire through the bodily lumen of a subject, advancing the guidewire in the bodily lumen to a treatment site, and removing the guidewire from the lumen. The insertion may also be facilitated by other accessories such as a delivery sheath, a push rod, a catheter, a pusher, a guide catheter, an endoscope, a cystoscope, or a fluoroscopy.

The insertion of a ureteral stent generally includes the steps of placing the ureteral stent over a long guidewire, and pushing the guidewire through the bladder, the ureter, and resting in the kidney of the subject. More specifically, one method of delivering a ureteral stent includes providing a ureteral stent which is detachably mounted over a distal end of a guidewire, the guidewire is pushed distally, typically from its proximal end, to advance the stent through the ureter in a direction toward the kidney by applying forward force internally against the anchor and closed distal end of the stent tip. A pusher may also be placed over the guidewire to help facilitate the process as disclosed, for example, in U.S. application publication No. US 2012/0,221,117. The ureteral stent may also be delivered with a guidewire plus a guide catheter, a push catheter and a handle assembly as disclosed, for example, in PCT application publication No. WO2014/151,615.

In some preferable aspects, a chitosan based ureteral stent as described herein may be inserted into the ureter of a subject by placing the stent over an elongated guidewire that traverses through bladder, ureter, and rests in kidney. In some more preferable aspects, a chitosan ureteral stent may be inserted over a guidewire into the kidney through a cystoscope. Advancement and placement of the chitosan ureteral stent may be confirmed using fluoroscopy. The guidewire is then removed leaving the chitosan based ureteral stent with a curl in the kidney and a curl in the bladder to prevent migration.

Methods for insertion, delivery, placement, or employment of a stent into a body lumen of a subject is well known in the art, for example, as disclosed in U.S. application publication No. US 2012/0,221,117, and PCT application publication Nos. WO 2006/127,092, WO 2014/116,718, WO2014/151,615, and WO 98/37,834.

The terms "surface hydrophilicity", "hydrophilicity", or "hydrophilic surface" as used herein are to mean a surface's ability to interact with or be dissolved by water and other polar substances. The terms "surface hydrophobicity", "hydrophobicity", or "hydrophobic surface" as used herein are to mean the tendency of a surface to exclude or remove water molecules. Surfaces having hydrophobic molecules tend to be non-polar and, thus, prefer other neutral molecules and non-polar solvents. Hydrophobic molecules in water often cluster together, forming micelles. Water on hydrophobic surfaces will exhibit a high contact angle. In contrast, Surfaces having hydrophilic molecules tend to be polar, and thus prefer polar solvents. Water on hydrophilic surfaces will exhibit a small contact angle. These contact angles can be measured by well-known methods. For example, static contact angle for flat surface could be measured with AST VCA systems. Dynamic contact angle for curve surface can be measured with Thermo Calm system. Contact angles for hydrophobic surface (or non-polar) are generally in the range of about 100 to about 170 degree. For example, poly-dimethylsioxane (PDMS) has a contact angle of 107.2 degree and polytetrafluoroethylene (PTFE) has a contact angle of 109.2 degree. Consequently, PDMS and PTFE are considered to be hydrophobic material. On the other hand, contact angles for hydrophilic surface (or polar) are generally in the range of about 20 to about 80 degree. For example, polyvinylpyrrolidone (PVP) has a contact angle of about 56 degree and polyacrylic acid (PAA) has a contact angle of between about 30 and about 63 degree. As a result, PVP and PAA are considered to be hydrophilic material.

In some embodiments of the invention, when the contact angle of a surface or material is measured at a value of between about 20 and about 80 degree, the surface or the material is considered to be hydrophilic. In some embodiments, when the contact angle of a surface or a material is measured at a value of about 20, 25, 30, 35, 40, 45, 50, 55, 60, 65, 70, 75, or about 80 degree, the surface or material is considered to be hydrophilic. En some embodiments, when the contact angle of a surface or a material is measured at a value of between about 100 and about 170 degree, the surface or the material is considered to be hydrophobic. In some embodiments, when the contact angle of a surface or a material is measured at a value of about 100, 105, 110, 115, 120, 125, 130, 135, 140, 145, 150, 155, 160, 165, or about 170 degree, the surface or material is considered to be hydrophobic. In some embodiments, a chitosan stent as described herein has a contact angle at a value of between about 20 and about 80 degrees. In some embodiments, a chitosan stent as described herein has a contact angle at a value of about 40, 41, 42, 43, 44, 45, 46, 47, 48, 49, 50, 51, 52, 53, 54, 55, 56, 57, 58, 59, or 60 degree.

"Surface hydrophilicity of a guidewire", "hydrophilicity of a guidewire", and similar expressions as used herein, all mean the hydrophilic properties of a guidewire. A guidewire is said to be hydrophilic if it has a hydrophilic surface. Or alternatively, the guidewire is called a hydrophilic guidewire. In general, the hydrophilicity of a guidewire should come from the material from which it is made. It may also come from its coating material if the guidewire is coated. Put it another way, the guidewire should be hydrophilic if its coating material is hydrophilic. Even more particularly, a coated guidewire is considered to be hydrophilic or have a hydrophilic surface if its coating material is measured at a value of between about 20 and about 80 degree.

"Surface hydrophobicity of a guidewire", "hydrophobicity of a guidewire", and similar expressions as used herein, all mean the hydrophobic properties of a guidewire. A guidewire is said to be hydrophobic if it has a hydrophobic surface. Or alternatively, the guidewire is called a hydrophobic guidewire. In general, the hydrophobicity of a guidewire should come from the material from which it is made. It may also come from its coating material if the guidewire is coated. Put it another way, the guidewire should be hydrophobic if its coating material is hydrophobic. Even more particularly, a coated guidewire is considered to be hydrophobic or have a hydrophobic surface if its coating material is measured at a value of between about 100 and about 170 degree.

"Surface hydrophilicity of a stent", "hydrophilicity of a stent", "hydrophilicity of a biodegradable stent", "hydrophilicity of a chitosan based stent" and similar expressions as used herein, all mean the hydrophilic properties of a stent. The hydrophilicity of a stent may come from its inner surface or its outer surface. In some embodiments of the invention, the hydrophilicity of the stent comes from the material from which it is made or from its coating material. Consequently, the stent should be hydrophilic if the coating material or the material from which it is made is hydrophilic. More particularly, a stent is considered to be hydrophilic or have a hydrophilic surface if the coating material or the material from which it is made has a contact angle measured at a value of between about 20 and about 80 degree.

"Surface hydrophobicity of a stent", "hydrophobicity of a stent", "hydrophobicity of a biodegradable stent", "surface hydrophobicity of a biodegradable stent" and similar expressions as used herein, all mean the hydrophobic properties of a stent. The hydrophobicity of a stent should come from the material from which it is made or from its coating material. Consequently, the stent should be hydrophobic if the coating material or the Material from which it is made is hydrophobic. More particularly, a stent is considered to be hydrophobic or have a hydrophobic surface if the coating material or the material from which it is made has a contact angle measured at a value of between about 100 and about 170 degree.

Hydrogel is used herein to mean a network of polymer chains that are hydrophilic, sometimes found as a colloidal gel in which water is the dispersion medium. Hydrogels are highly absorbent (they can contain over 90% water) natural or synthetic polymeric networks. Hydrogels also possess a degree of flexibility very similar to natural tissue, due to their significant water content. Hydrogels may be synthesized in a number of chemical ways. These include one-step procedures like polymerization and parallel cross-linking of multifunctional monomers, as well as multiple step procedures involving synthesis of polymer molecules having reactive groups and their subsequent cross-linking, possibly also by reacting polymers with suitable cross-linking agents. Hydrogel polymer networks can be designed and synthesized with molecular-scale control over structure such as cross-linking density and with tailored properties, such as biodegradation, mechanical strength, and chemical and biological response to stimuli.

In some aspects of the invention, the biodegradable stents may further contain one or more therapeutic agents. In some aspects, the one or more therapeutic agents are selected from a group consisting of analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, antiplatelet agents and antibacterial agents, antiviral agents, antimicrobials, antiinfectives, and combination thereof.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

One object of the invention is to provide a method of properly deploying a biodegradable stent into a treatment site of a subject. Another object of the invention is to provide a method of properly deploying a chitosan based biodegradable stent into a treatment site of a subject. Yet another object of the invention is to provide a method of properly deploying a biodegradable ureteral stent into a treatment site of a subject. Still yet another object of the invention is to provide a method of properly deploying a biodegradable ureteral stent into the ureter of a subject to allow urine drainage, and/or pressure relief, and/or removal of kidney stones, and/or treatment of ureter obstructions or impairments. Yet another object of the invention is to provide a method of properly deploying a chitosan based ureteral stent into a ureter of a subject to allow urine drainage, and/or pressure relief, and/or removal of kidney stones, and/or for treatment of ureter obstructions or impairments.

The embodiments of the present invention relate generally to methods, systems, and kits for deploying biodegradable stents into a treatment site of a subject. More particularly, the embodiments of the present invention relate to methods, systems, and kits for deploying a biodegradable ureteral stent into a treatment site of a patient. Even more particularly, the embodiments of the present invention relate to methods, systems, and kits for deploying a biodegradable chitosan based ureteral stent into the ureter of a subject for the purpose of urinary drainage from the kidney to the bladder, and/or for pressure relief, and/or for removal of kidney stones, and/or for treatment of ureter obstructions or impairments.

In one embodiment, the present invention provides a method of identifying a guidewire for a proper delivery of a biodegradable stent into a treatment site of a subject, the method comprising determining the surface hydrophilicity or surface hydrophobicity of the guidewire; and determining the surface hydrophilicity or surface hydrophobicity of the biodegradable stent, wherein the guidewire is likely proper for the delivery of the biodegradable stent into the treatment site of the subject when the guidewire and the stent both have a hydrophilic surface or both have a hydrophobic surface. In some embodiments, the surface hydrophilicity or hydrophobicity of the biodegradable stent and/or the guidewire are determined by measuring their respective surface tensions. In some embodiments, the surface hydrophilicity or hydrophobicity of the biodegradable stent and/or the guidewire are determined by measuring their respective contact angles. In some embodiments, the method comprising determining the contact angle of the guidewire, and determining the contact angle of the biodegradable stent, wherein the guidewire is likely proper for the delivery of the stent when both of their contact angles are at a value of between about 100 and about 170 degree. In some embodiments, the method comprising determining the contact angle of the guidewire, and determining the contact angle of the biodegradable stent, wherein the guidewire is likely proper for the delivery of the stent when both of their contact angles are at a value of between about 20 and about 80 degree.

In one embodiment, the invention provides a method of identifying a guidewire for a proper delivery of a biodegradable ureteral stent into a treatment site of a subject; the method comprising determining the surface hydrophilicity or surface hydrophobicity of the guidewire; and determining the surface hydrophilicity or surface hydrophobicity of the biodegradable ureteral stent, wherein the guidewire is likely proper for the delivery of the biodegradable ureteral stent into the treatment site of the subject when the guidewire and the biodegradable ureteral stent both have a hydrophilic surface or both have a hydrophobic surface. In some embodiments, the surface hydrophilicity or hydrophobicity of the biodegradable ureteral stent and/or the guidewire are determined by measuring their respective surface tensions. In some embodiments, the surface hydrophilicity or hydrophobicity of the biodegradable ureteral stent and/or the guidewire are determined by measuring their respective contact angles. In some embodiments, the method comprising determining the contact angle of the guidewire, and determining the contact angle of the biodegradable ureteral stent, wherein the guidewire is likely proper for the delivery of the stent when both of their contact angles are at a value of between about 100 and about 170 degree. In some embodiments, the method comprising determining the contact angle of the guidewire, and determining the contact angle of the biodegradable ureteral stent, wherein the guidewire is likely proper for the delivery of the stent when both of their contact angles are at a value of between about 20 and about 80 degree.

In one embodiment, the invention provides a method of identifying a guidewire for the proper delivery of a chitosan based stent into a treatment site of a subject; the method comprising determining the surface hydrophilicity or surface hydrophobicity of the guidewire; and determining the surface hydrophilicity or surface hydrophobicity of the chitosan based stent, wherein the guidewire is likely proper for the delivery of the chitosan based stent into the treatment site of the subject when the guidewire and the chitosan based stent both have a hydrophilic surface or both have a hydrophobic surface. In some embodiments, the surface hydrophilicity or hydrophobicity of the chitosan based stent and/or the guidewire are determined by measuring their respective surface tensions. In some embodiments, the surface hydrophilicity or hydrophobicity of the chitosan based stent and/or the guidewire are determined by measuring their respective contact angles. In some embodiments, the method comprising determining the contact angle of the guidewire, and determining the contact angle of the chitosan based stent, wherein the guidewire is likely proper for the delivery of the chitosan based stent when both of their contact angles are at a value of between about 20 and about 80 degree. In some embodiments, a hydrogel coated guidewire may be proper for the delivery of a chitosan based stent. In some embodiments, an E-Z Glider® guidewire may be proper for the delivery of a chitosan based stent. In some embodiments, a 0.038" E-Z Glider® guidewire may be proper for the delivery of a chitosan based stent.

In one embodiment, the invention provides a method of identifying a guidewire for a proper delivery of a chitosan based ureteral stent into the ureter of a subject for the purpose of urinary drainage from the kidney to the bladder, and/or pressure relief, and/or removal of kidney stones, and/or for the treatment of ureter obstructions or impairments; the method comprising determining the surface hydrophilicity or surface hydrophobicity of the guidewire; and determining the surface hydrophilicity or surface hydrophobicity of the chitosan based ureteral stent, wherein the guidewire is likely proper for the delivery of the chitosan based ureteral stent into a treatment site of the subject when the guidewire and the chitosan based ureteral stent both have a hydrophilic surface or both have a hydrophobic surface. In some embodiments, the surface hydrophilicity or hydrophobicity of the chitosan based ureteral stent and/or the guidewire are determined by measuring their respective surface tensions. In some embodiments, the surface hydrophilicity or hydrophobicity of the chitosan based ureteral stent and/or the guidewire are determined by measuring their respective contact angles. In some embodiments, the method comprising determining the contact angle of the guidewire, and determining the contact angle of the chitosan based ureteral stent, wherein the guidewire is likely proper for the delivery of the chitosan based stent when both of their contact angles are at a value of between about 20 and about 80. In some embodiments, a hydrogel coated guidewire may be proper for the delivery of a chitosan based ureteral stent. In some embodiments, an E-Z Glider® guidewire may be proper for the delivery of a chitosan based ureteral stent. In some embodiments, a 0.038" E-Z Glider® guidewire may be proper for the delivery of a chitosan based ureteral stent.

In one embodiment, the invention provides a method of properly delivering a biodegradable stent into a treatment site of a subject, the method comprising determining the surface hydrophilicity or surface hydrophobicity of a guidewire; determining the surface hydrophilicity or surface hydrophobicity of a biodegradable stent, wherein the guidewire is likely proper for the delivery of the stent into the treatment site of the subject when the guidewire and the stent both have a hydrophilic surface or both have a hydrophobic surface; and inserting the biodegradable stent with the identified guidewire into the treatment site of the patient. In some embodiments, the surface hydrophilicity or hydrophobicity of the biodegradable stent and/or the guidewire are determined by measuring their respective surface tensions. In some embodiments, the surface hydrophilicity or hydrophobicity of the biodegradable stent and/or the guidewire are determined by measuring their respective contact angles. In some embodiments, the method comprising determining the contact angle of the guidewire, and determining the contact angle of the biodegradable stent, wherein the guidewire is likely proper for the delivery of the stent when both of their contact angles are at a value of between about 100 and about 170 degree; and inserting the biodegradable stent with the identified guidewire into the treatment site of the patient. In some embodiments, the method comprising determining the contact angle of the guidewire, and determining the contact angle of the biodegradable stent, wherein the guidewire is likely proper for the delivery of the stent when both of their contact angles are at a value of between about 20 and about 80 degree, and inserting the biodegradable stent into the treatment site of the patient using the identified guidewire.

In one embodiment, the invention provides a method of properly delivering a biodegradable ureteral stent into a treatment site of a subject, the method comprising determining the surface hydrophilicity or surface hydrophobicity of a guidewire; determining the surface hydrophilicity or surface hydrophobicity of a biodegradable ureteral stent, wherein the guidewire is likely proper for the delivery of the ureteral stent into the treatment site of the subject when the guidewire and the ureteral stent both have a hydrophilic surface or both have a hydrophobic surface; and inserting the biodegradable ureteral stent with the identified guidewire into the treatment site of the patient. In some embodiments, the surface hydrophilicity or hydrophobicity of the biodegradable ureteral stent and/or the guidewire are determined by measuring their respective surface tensions. In some embodiments, the surface hydrophilicity or hydrophobicity of the biodegradable ureteral stent and/or the guidewire are determined by measuring their respective contact angles. In some embodiments, the method comprising determining the contact angle of the guidewire; determining the contact angle of the biodegradable ureteral stent, wherein the guidewire is likely proper for the delivery of the stent when both of their contact angles are at a value of between about 100 and about 170 degree; and inserting the biodegradable ureteral stent with the identified guidewire into the treatment site of the patient. In some embodiments, the method comprising determining the contact angle of the guidewire; determining the contact angle of the biodegradable ureteral stent, wherein the guidewire is likely proper for the delivery of the stent when both of their contact angles are at a value of between about 20 and about 80 degree; and inserting the biodegradable ureteral stent into the treatment site of the patient using the identified guidewire.

In one embodiment, the invention provides a method of properly delivering a chitosan based stent into a treatment site of a subject, the method comprising determining the surface hydrophilicity or surface hydrophobicity of a guidewire; determining the surface hydrophilicity or surface hydrophobicity of a chitosan based stent, wherein the guidewire is likely proper for the delivery of the chitosan based stent into the treatment site of the subject when the guidewire and the chitosan based stent both have a hydrophilic surface or both have a hydrophobic surface; and inserting the chitosan based stent with the identified guidewire into the treatment site of the patient. In some embodiments, the surface hydrophilicity or hydrophobicity of the chitosan based stent and/or the guidewire are determined by measuring their respective surface tensions. In some embodiments, the surface hydrophilicity or hydrophobicity of the chitosan based stent and/or the guidewire are determined by measuring their respective contact angles. In some embodiments, the method comprising determining the contact angle of the guidewire; determining the contact angle of the chitosan based stent, wherein the guidewire is likely proper for the delivery of the chitosan based stent when both of their contact angles are at a value of between about 20 and about 80 degree; and inserting the chitosan based stent into the treatment site of the patient using the identified guidewire. In some embodiments, a hydrogel coated guidewire may be proper for the delivery of a chitosan based stent. In some embodiments, an E-Z Glider® guidewire may be proper for the delivery of a chitosan based stent. In some embodiments, a 0.038" E-Z Glider® guidewire may be proper for the delivery of a chitosan based stent.

In one embodiment, the invention provides a method of properly delivering a chitosan based ureteral stent into a subject's ureter, the method comprising determining the surface hydrophilicity or surface hydrophobicity of a guidewire; determining the surface hydrophilicity or surface hydrophobicity of a chitosan based ureteraol stent, wherein the guidewire is likely proper for the delivery of the chitosan based ureteral stent into the subject's ureter when the guidewire and the chitosan based ureteral stent both have a hydrophilic surface or both have a hydrophobic surface; and inserting the chitosan based stent into the ureter of the subject using the identified guidewire. In some embodiments, the surface hydrophilicity or hydrophobicity of the chitosan based ureteral stent and/or the guidewire are determined by measuring their respective surface tensions. In some embodiments, the surface hydrophilicity or hydrophobicity of the chitosan based ureteral stent and/or the guidewire are determined by measuring their respective contact angles. In some embodiments, the method comprising determining the contact angle of the guidewire; determining the contact angle of the chitosan based ureteral stent, wherein the guidewire is likely proper for the delivery of the chitosan based stent when both of their contact angles are at a value of between about 20 and about 80 degree; and inserting the chitosan based stent into the ureter of the subject using the identified guidewire. In some embodiments, a hydrogel coated guidewire may be proper for the delivery of a chitosan based stent. In some embodiments, an E-Z Glider® guidewire may be proper for the delivery of a chitosan based ureteral stent. In some embodiments, a 0.038" E-Z Glider® guidewire may be proper for the delivery of a chitosan based ureteral stent.

In one embodiment, the present invention provides a kit for a proper delivery of a biodegradable stent into a treatment site of a subject; the kit comprising a guidewire, a biodegradable stent, and instructions for measuring surface hydrophilicity or surface hydrophobicity of a guidewire and a biodegradable stent. The kit may further comprise instructions for using a guidewire to insert a stent to a treatment site of the subject. In some embodiments, the kit may include instructions for measuring surface tensions of both a guidewire and a biodegradable stent. In some embodiments, the kit may include instructions for measuring contact angles of both a guidewire and a biodegradable stent. In some embodiments, the kit may include additional accessories and instructions thereof.

In one embodiment, the invention provides a kit for a proper delivery of a biodegradable ureteral stent into a treatment site of a subject, the kit comprising a guidewire, a biodegradable ureteral stent, and instructions for measuring surface hydrophilicity or surface hydrophobicity of a guidewire and a biodegradable ureteral stent. The kit may further comprise instructions for using a guidewire to insert a ureteral stent to a treatment site of the subject. In some embodiments, the kit may include instructions for measuring surface tensions of both a guidewire and a ureteral stent. In some embodiments, the kit may include instructions for measuring contact angles of both a guidewire and a ureteral stent. In some embodiments, the kit may include additional accessories and instructions thereof.

In one embodiment, the invention provides a kit for a proper delivery of a chitosan based stent into a treatment site of a subject, the kit comprising a guidewire, a chitosan based stent, and instructions for measuring surface hydrophilicity or surface hydrophobicity of a guidewire and a chitosan based stent. The kit may further comprise instructions for using a guidewire to insert a chitosan based stent to a treatment site of the subject. In some embodiments, the kit may include instructions for measuring surface tensions of both a guidewire and a chitosan based stent. In some embodiments, the kit may include instructions for measuring contact angles of both a guidewire and a chitosan based stent. In some embodiments, the kit may include additional accessories and instructions thereof.

In yet another embodiment, the invention provides a kit for a proper delivery of a chitosan based ureteral stent into a subject's ureter for the purpose of urinary drainage from the kidney to the bladder, the kit comprising a guidewire, a biodegradable stent, and instructions for measuring surface hydrophilicity or surface hydrophobicity of the guidewire and the chitosan based ureteral stent. The kit may further comprise instructions for using a guidewire to insert a chitosan based ureteral stent to a treatment site of the subject. In some embodiments, the kit may include instructions for measuring surface tensions of both a guidewire and a chitosan based ureteral stent. In some embodiments, the kit may include instructions for measuring contact angles of both a guidewire and a chitosan based ureteral stent. In some embodiments, the kit may include additional accessories and instructions thereof.

In one embodiment, the present invention provides a biodegradable stent delivery system, the system comprising a biodegradable stent, a guidewire, and other accessories. In some embodiments, the other accessories may include a pusher, or a guide catheter, or a push catheter, or a delivery sheath, or a cystoscope, or an endoscope. In some embodiments, the system may comprise further instruments, device or equipment for measuring surface tensions, and/or measuring contact angles. The system may further comprise a kit for identifying a guidewire for a proper delivery of a biodegradable stent into a treatment site of a subject wherein the guidewire is likely proper for the delivery of the stent when the guidewire surface and the stent surface are determined to be both hydrophilic or both hydrophobic.

In one embodiment, the invention provides a biodegradable ureteral stent delivery system, the system comprising a biodegradable ureteral stent, a guidewire, and other accessories. In some embodiments, the other accessories may include a pusher, or a guide catheter, or a push catheter, or a delivery sheath, or cystoscope, or an endoscope. In some embodiments, the system may comprise further instruments, device or equipment for measuring surface tensions, and/or measuring contact angles. The system may further comprise a kit for identifying a guidewire for a proper delivery of a biodegradable ureteral stent into a treatment site of a subject wherein the guidewire is likely proper for the delivery of the ureteral stent when the guidewire surface and the ureteral stent surface are determined to be both hydrophilic or both hydrophobic.

In one embodiment, the invention provides a chitosan based stent delivery system, the system comprising a chitosan based stent, a suitable guidewire, and other accessories. In some embodiments, the other accessories may include a pusher, or a guide catheter, or a push catheter, or a delivery sheath, or cystoscope, or an endoscope. In some embodiments, the system may comprise further instruments, device or equipment for measuring surface tensions, and/or measuring contact angles. The system may further comprise a kit for identifying a guidewire for a proper delivery of a chitosan based stent into a treatment site of a subject wherein the guidewire is likely proper for the delivery of the chitosan based stent when the guidewire surface and the chitosan based stent surface are determined to be both hydrophilic.

In yet another embodiment, the invention provides a chitosan based ureteral stent delivery system, the system comprising a chitosan based ureteral stent, a guidewire, and other accessories. In some embodiments, the other accessories may include a pusher, or a guide catheter, or a push catheter, or a delivery sheath, or cystoscope, or an endoscope. In some embodiments, the system may comprise further instruments, device or equipment for measuring surface tensions, and/or measuring contact angles. The system may further comprise a kit for identifying a guidewire for a proper delivery of a chitosan based ureteral stent into a treatment site of a subject wherein the guidewire is likely proper for the delivery of the chitosan based ureteral stent when the guidewire surface and the chitosan based stent ureteral surface are determined to be both hydrophilic.

In some embodiments, the invention further provides a method of treating urological related diseases or conditions with a biodegradable stent, the method comprising providing a proper guidewire in accordance with a determination of the surface hydrophilicity or surface hydrophobicity of the biodegradable stent and/or the guidewire; and inserting the biodegradable stent into the treatment site of a subject using the provided guidewire. In some embodiments, the urological related disease is a kidney related disease. In some embodiments, the treatment is for kidney urine drainage. In some embodiments, the treatment is for kidney pressure relief. In some embodiments, the treatment is for removal of kidney stones. In some embodiments, the treatment is for ureter obstructions or impairments. In some embodiments, the surface hydrophilicity or hydrophobicity of the stent and/or the guidewire are determined by their respective surface tensions. In some embodiments, the surface hydrophilicity or hydrophobicity of the biodegradable stent and/or the guidewire are determined by their respective contact angles. In some embodiments, the guidewire is likely proper for the delivery of the biodegradable stent when the biodegradable stent has a contact angle at a value of between about 100 and about 170 degree, and the guidewire has a contact angle at a value of between about 100 and about 170 degree. In some embodiments, the guidewire is likely proper for the delivery of the biodegradable stent when the biodegradable stent has a contact angle at a value of between about 20 and about 80 degree, and the guidewire has a contact angle at a value of between about 20 and about 80 degree. In some embodiments, the biodegradable stent further contains one or more therapeutic agents. In some embodiments, the one or more therapeutic agents are selected form analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, antiplatelet agents and antibacterial agents, antiviral agents, antimicrobials, antiinfectives, and combination thereof.

In some embodiments, the invention further provides a method of treating urological related diseases or conditions with a biodegradable ureteral stent, the method comprising providing a proper guidewire in accordance with a determination of the surface hydrophilicity and/or surface hydrophobicity of the biodegradable ureteral stent and/or the guidewire; and inserting the biodegradable ureteral stent into the treatment site of a subject using the provided guidewire. In some embodiments, the urological disease is a kidney related disease. In some embodiments, the treatment is for urine drainage. In some embodiments, the treatment is for pressure relief. In some embodiments, the treatment is for removal of kidney stones. In some embodiments, the treatment is for ureter obstructions or impairments. In some embodiments, the surface hydrophilicity or hydrophobicity of the biodegradable ureteral stent and/or the guidewire are determined by their respective surface tensions. In some embodiments, the surface hydrophilicity or hydrophobicity of the biodegradable ureteral stent and/or the guidewire are determined by their respective contact angles. In some embodiments, the guidewire is likely proper for the delivery of the biodegradable ureteral stent when the biodegradable ureteral stent has a contact angle at a value of between about 100 and about 170 degree, and the guidewire has a contact angle at a value of between about 100 and about 170 degree. In some embodiments, the guidewire is likely proper for the delivery of the biodegradable ureteral stent when the biodegradable stent has a contact angle at a value of between about 20 and about 80 degree, and the guidewire has a contact angle at a value of between about 20 and about 80 degree. In some embodiments, the biodegradable stent further contains one or more therapeutic agents. In some embodiments, the one or more therapeutic agents are selected form analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, antiplatelet agents and antibacterial agents, antiviral agents, antimicrobials, antiinfectives, and combination thereof.

In some embodiments, the invention further provides a method of treating urological related diseases or conditions with a chitosan based stent, the method comprising identifying a proper guidewire in accordance with a determination of the surface hydrophilicity or surface hydrophobilicy of the chitosan based stent and the guidewire; and inserting the chitosan based stent into a treatment site of a subject using the properly identified guidewire. In some embodiments, the urological disease is a kidney related disease. In some embodiments, the treatment is for urine drainage. In some embodiments, the treatment is for pressure relief. In some embodiments, the treatment is for removal of kidney stones. In some embodiments, the treatment is for ureter obstructions or impairments. In some embodiments, the surface hydrophilicity or hydrophobicity of the stent and/or the guidewire are determined by their respective surface tensions. In some embodiments, the surface hydrophilicity or hydrophobicity of the chitosan stent and/or the guidewire are determined by their respective contact angles. In some embodiments, the guidewire is likely proper for the delivery of the chitosan stent when the chitosan stent has a contact angle at a value of between about 20 and about 80 degree, and the guidewire has a contact angle at a value of between about 20 and about 80 degree. In some embodiments, the guidewire is likely proper for the delivery of the chitosan sent when the chitosan based stent has a chitosan content in the amount of from about 60 to about 90 weight percentage of the total stent weight, and the guidewire has a contact angle at a value of between about 20 and about 80. In some embodiments, the chitosan based stent further contains one or more therapeutic agents. In some embodiments, the one or more therapeutic agents are selected form analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, antiplatelet agents and antibacterial agents, antiviral agents, antimicrobials, antiinfectives, and combination thereof.

In some embodiments, the invention further provides a method of treating urological or kidney related diseases with a chitosan based ureteral stent, the method comprising identifying a proper guidewire in accordance with its surface hydrophilicity or surface hydrophobilicy; and inserting the chitosan based stent into a treatment site of a subject using the properly identified guidewire. In some embodiments, the urological related disease is a kidney related disease. In some embodiments, the treatment is for kidney urine drainage. In some embodiments, the treatment is for kidney pressure relief in some embodiments, the treatment is for removal of kidney stones. In some embodiments, the treatment is for ureter obstructions or impairments. In some embodiments, the surface hydrophilicity or hydrophobicity of the chitosan ureteral stent and/or the guidewire are determined by their respective surface tensions. In some embodiments, the surface hydrophilicity or hydrophobicity of the chitosan ureteral stent and/or the guidewire are determined by their respective contact angles. In some embodiments, the guidewire is likely proper for the delivery of the chitosan ureteral stent when the chitosan ureteral stent has a contact angle at a value of between about 20 and about 80 degree, and the guidewire has a contact angle at a value of between about 20 and about 80 degree. In some embodiments, the chitosan based ureteral stent contains one or more therapeutic agents. In some embodiments, the one or more therapeutic agents are selected form analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, antiplatelet agents and antibacterial agents, antiviral agents, antimicrobials, antiinfectives, and combination thereof.

In some specific embodiments, the analgesics/antipyretics include medicines such as salicylates, morphine, oxycodone, codeine, hydrocodone, dihydromorphine, pethidine, ibuprofen, aspirin, naproxen, ketoprofen, and nimesulide. The antiasthamatics include medicines such as beclometasone dipropionate, budesonide, fluticasone, salmeterol, hexoprenaline, isoprenaline, mometasone/formoterol, mometasone furoate, omalizumab, pirquinozol, pitrakinra, prednisone, reproterol, salbutamol, tranilast. The antibiotics include penicillins, cephalosporins, polymyxins, rifamycins, lipiarmycins, quinolones, and sulfonamides, macrolides, lincosamides, tetracyclines, aminoglycosides, daptomycin, glycylcyclines, tigecycline, oxazolidinones, linezolid, lipiarmycins, fidaxomicin. The antidepressants include medicines such as sertraline, citalopram, fluoxetine, escitalopram, trazodone, duloxetine, Paroxetine, amitriptyline, venlafaxine, bupropion, mirtazapine, desvenlafaxine, nortriptyline. The antidiabetics include tolbutamide, acetohexamide, tolazamide, chlorpropamide, glipizide, glyburide or glibenclamide, glimepiride, gliclazide, glycopyramide, gliquidone, rosiglitazone, pioglitazone, troglitazone, metformin, phenformin, buformin, meglitinides, repaglinide, nateglinide, miglitol, acarbose, voglibose, exenatide, liraglutide, taspoglutide, canagliflozin, and dapagliflozin. The antifungal agents include amphotericin B, candicidin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, ciclopirox, flucytosine, or 5-fluorocytosine, griseofulvin, haloprogin, tolnaftate. The antihypertensive agents include atenolol, metoprolol, nadolol, nebivolol, oxprenolol, pindolol, propranolol, timolol, doxazosin, phentolamine, indoramin, phenoxybenzamine, prazosin, terazosin, tolazoline, bucindolol, carvedilol, labetalol, benzodiazepines, amlodipine, cilnidipine, felodipine, isradipine, lercanidipine, levamlodipine, nicardipine, nifedipine, nimodipine, nitrendipine, diltiazem, verapamil, captopril, enalapril, fosinopril, lisinopril, perindopril, quinapril, ramipril, trandolapril, benazepril, candesartan, eprosartan, irbesartan, losartan, olmesartan, telmisartan, valsartan, eplerenone, spironolactone, clonidine, guanabenz, guanfacine, methyldopa, moxonidine.

In some embodiments, the invention provides a method of delivering a chitosan based ureteral stent into a ureter of a patient for the treatment of urine drainage, and/or pressure relief, and/or removal of kidney stones, and/or treatment of ureter obstructions or impairments, the method comprising providing a proper guidewire, hydrating the chitosan based ureteral stent; and inserting the chitosan based ureteral stent into the ureter of the patient using the identified guidewire. In some of the embodiments, the guidewire is proper when it has a contact angle at a value of between about 20 and about 80 degree. In some embodiments, a hydrogel guidewire is likely proper when the chitosan based ureteral stent has a contact angle at a value of between about 20 and about 80 degree. In some embodiments, an E-Z Glider® guidewire is likely proper when the chitosan based ureteral stent has a contact angle at a value of between about 20 and about 80 degree. In some embodiments, the guidewire is proper when it has a contact angle at a value of between about 20 and about 80 degree and the chitosan based ureteral stent has a contact angle at a value of between about 40 and about 60 degree. In some embodiments, a hydrogel guidewire is likely proper when the chitosan based ureteral stent has a contact angle at a value of between about 40 and about 60 degree. In some embodiments, an E-Z Glider® guidewire is likely proper when the chitosan based ureteral stent has a contact angle at a value of between about 40 and about 60 degree.

In some embodiments, the guidewire is likely proper when it has a contact angle at a value of between about 20 and about 80 degree wherein the chitosan ureteral stent has a chitosan content in the amount of from about 60 to about 90 weight percentage of the total stent weight. In some embodiments, a hydrogel guidewire is likely proper when the chitosan based ureteral stent has a chitosan content in the amount of from about 60 to about 90 weight percentage of the total stent weight. In some embodiments, an E-Z Glider® guidewire is likely proper when the chitosan based ureteral stent has a chitosan content in the amount of from about 60 to about 90 weight percentage of the total stent weight. In some embodiments, the guidewire is likely proper when it has a contact angle at a value of between about 20 and about 80 degree wherein the chitosan ureteral stent has a chitosan content in the amount of from about 70 to about 85 weight percentage of the total stent weight. In some embodiments, a hydrogel guidewire is likely proper when the chitosan based ureteral stent has a chitosan content in the amount of from about 70 to about 85 weight percentage of the total stent weight. In some embodiments, an E-Z Glider® guidewire is likely proper when the chitosan based ureteral stent has a chitosan content in the amount of from about 70 to about 85 weight percentage of the total stent weight.

In some embodiments, the chitosan based ureteral stent may contain chitosan in an amount of between about 60 and about 90 weight percentage of the total stent weight. In some embodiments, the chitosan based ureteral stent may contain chitosan in an amount of between about 70 and about 85 weight percentage of the total stent weight. In some embodiments, the chitosan based ureteral stent may contain chitosan in an amount of between about 75 and about 80 weight percentage of the total stent weight. In some embodiments, the chitosan based ureteral stent may contain about barium sulfate in an amount of between about 15 and about 30 weight percentage of the total stent weight. In some embodiments, the chitosan based ureteral stent may contain about barium sulfate in the amount of between about 20 and about 25 weight percentage of the total stent weight. In some embodiments, the chitosan based ureteral stent may have a degree of acetylation of between about 5 and about 30. In some embodiments, the chitosan based ureteral stent may have a degree of acetylation of between about 10 and about 20. In some embodiments, the chitosan based ureteral stent may have a degree of acetylation of about 16.3.

In some embodiments, the chitosan based ureteral stent may have a length at a value of between 21 cm and 26 cm. In some embodiments, the chitosan based ureteral stent may have a length of about 24.6 cm or 21.9 cm. In some embodiments, the chitosan based ureteral stent may have a length at a value of between 24.55 cm and 24.65 cm. In some embodiments, the chitosan based ureteral stent may have a length at a value of between 20.85 cm and 21.95 cm.

In some embodiments, the chitosan based ureteral stent has a wet outer diameter at a value of between about 2 mm and about 3 mm. In some embodiments, the chitosan based ureteral stent has a wet outer diameter at a value of between 2.17 mm and 2.25 mm. In some embodiments, the chitosan based ureteral stent has a wet internal diameter at a value of between about 1 mm and about 2 mm. In some embodiments, the chitosan based ureteral stent has a wet internal diameter at a value of between 1.02 mm and 1.08 mm. In some embodiments, the chitosan based ureteral stent has a wall thickness at a value of between about 0.2 mm and about 0.8 mm. In some embodiments, the chitosan based ureteral stent has a wall thickness at a value of between about 0.4 mm and about 0.6 mm. In some embodiments, the chitosan based ureteral stent has a wall thickness at a value of about 0.58 mm.

In some embodiments, the chitosan based ureteral stent may be pre-hydrated. In some embodiments, the chitosan based ureteral stent may be pre-hydrated for 5, 10, 15, 20, 25, or 30 minutes before being used or delivered. In some embodiments, the chitosan based ureteral stent may be used in any physiological conditions of a subject. In some preferable embodiments, the chitosan based ureteral stent may achieve the best results when used when the urine of a subject is adjusted to a pH range between about 6 and about 8. In some of the embodiments, the treatment method may comprise adjusting the urine pH of a patient before treatment. In some embodiments, the chitosan based ureteral stent degrade inside the body lumen of the subject in about 1 week. In some embodiments, the chitosan based ureteral stent degrade inside the body lumen of the subject in about 2 weeks. In some embodiments, the chitosan based ureteral stent degrade inside the body lumen of the subject in about 3 weeks. In some embodiments, the chitosan based ureteral stent degrade inside the body lumen of the subject in about 4 weeks. In some embodiments, the chitosan based ureteral stent degrade inside the body lumen of the subject in about 1 month. In some embodiments, the chitosan based ureteral stent degrade inside the body lumen of the subject in about 2 months. In some embodiments, the chitosan based ureteral stent degrade inside the body lumen of the subject in about 3-4 months.

In some embodiments, the invention further provides a method of treating urological or kidney related diseases with a biodegradable chitosan based, thereby obviating a problem of removing these stents from a treatment site, and consequently saving medical costs. In some embodiments, the invention provides a method of saving medical cost in treating urological or kidney related diseases or conditions, the method comprising providing a biodegradable stent, and inserting the biodegradable stent into a treatment site of a subject without further or a secondary surgery, thereby saving medical cost. In some embodiments, the invention provides a method for treating urological or kidney related diseases or conditions by utilizing a biodegradable chitosan stent in a controllable rate of degradation of the chitosan stent. In some embodiments, the invention provides a method for treating urological or kidney related diseases or conditions by utilizing a biodegradable and biocompatible chitosan stent to assure a safe and innocuous disappearance of the stent without the need for a second surgical procedure for its removal after it has completed its function.

EXAMPLES

Example 1

Figure 2:
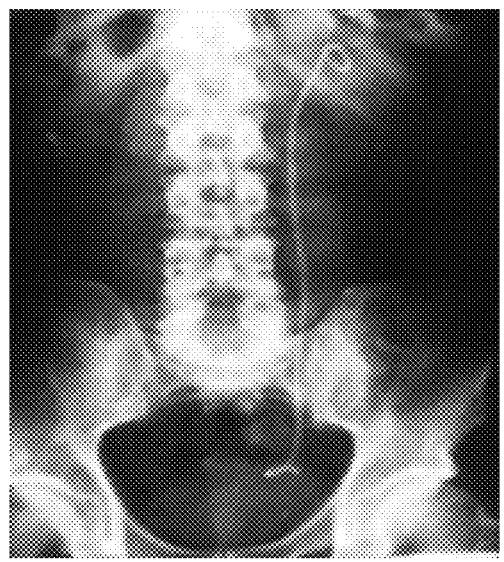
FIG. 2 is an X-ray picture showing an indwelling ureteral stent with 2 "pigtail curls" that anchor the device between the kidney and the bladder of a patient.
Figure 3:
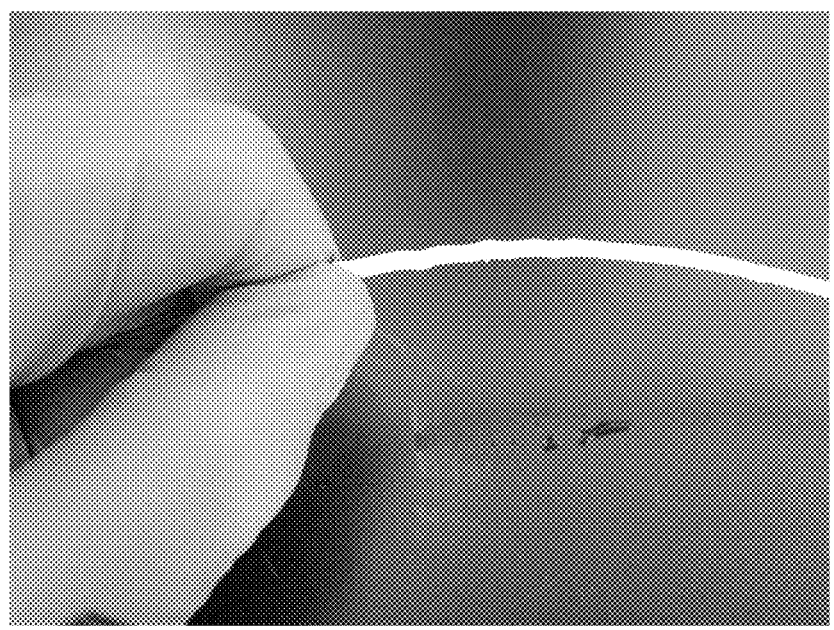
FIG. 3 shows that the chitosan stent buckled when using a polytetrafluoroethylene (PTFE) coated guidewire, a standard procedure for a ureteral stent insertion.
Figure 4:
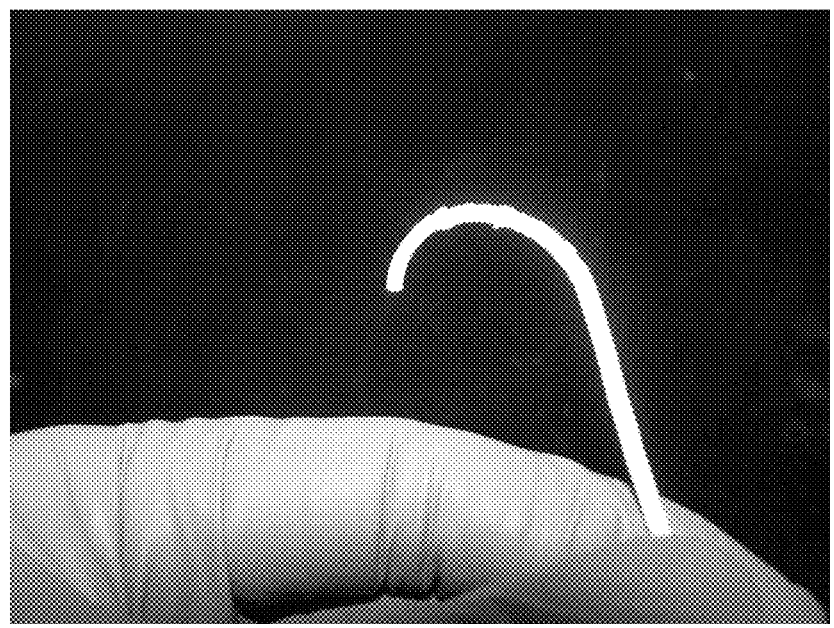
FIG. 4 shows that the chitosan stent recoiled when using a PTFE coated guidewire for insertion.

FIG. 1 illustrates what a ureteral stent should look like when it is properly positioned between the kidney and the bladder after it passes through ureter. FIG. 2 is an X-ray picture of a properly positioned ureteral stent in a real situation. It can be seen from the picture that the two ends of the stent are properly stationed in the kidney and in the bladder, and the stent is properly stretched without any damage. FIG. 3 shows that the chitosan stent buckled when using a 0.035" or a 0.038" PTFE coated guidewire for the pushing. FIG. 4 shows that the chitosan stent recoiled when using a PTFE coated guild wire for the pushing. PTFE coated guidewires are the conventionally used guidewires for pushing a ureteral stent through the urological system to place the stent. These examples show that using PTFE coated guidewires to place the chitosan based stents damages the stents. Consequently, these PTFE guidewires are not suitable for placing the chitosan based stents into a proper position between the kidney and the bladder of a subject.

Example 2

Figure 5:
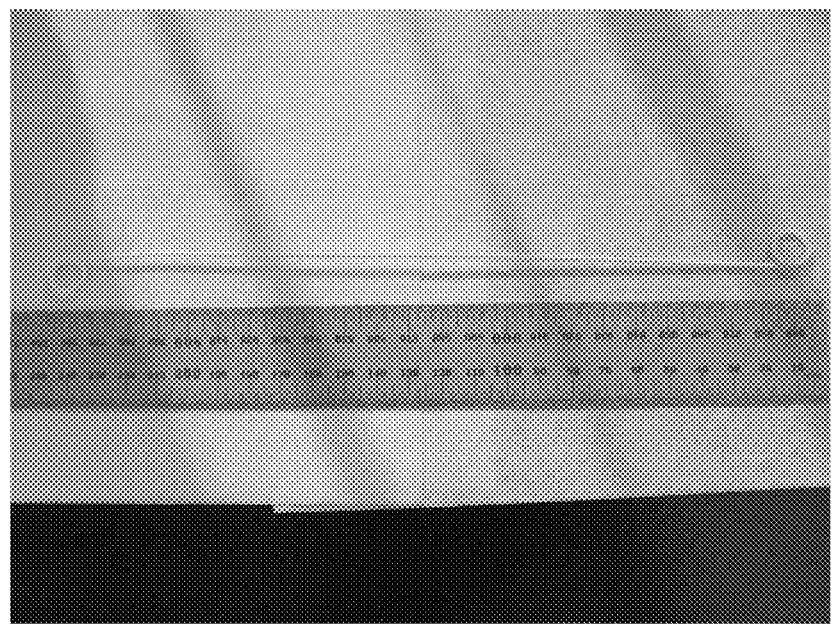
FIG. 5 shows a chitosan ureteral stent with a pigtail on either end of the stent before it's hydrated.
Figure 6:
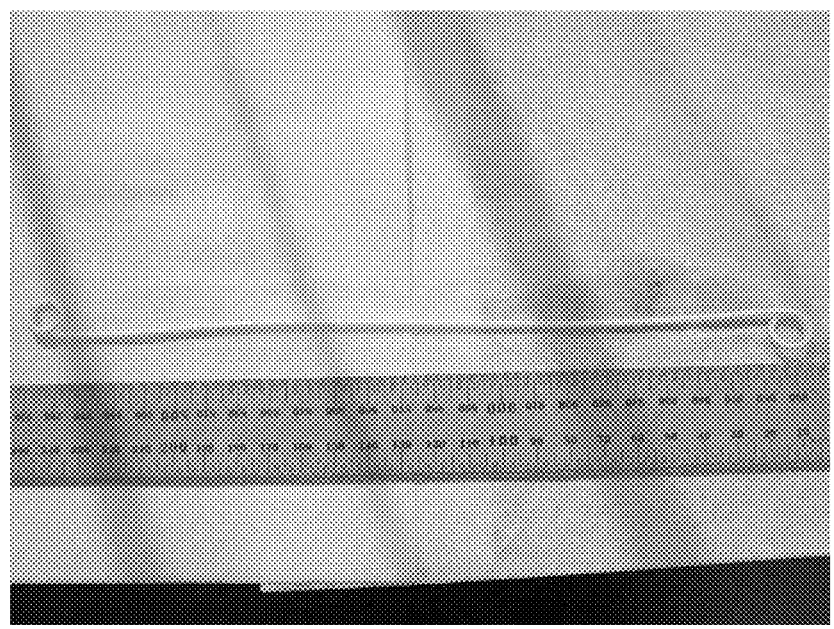
FIG. 6 shows a chitosan ureteral stent with a pigtail on either end of the stent after it's hydrated.

FIG. 5 shows a chitosan ureteral stent in its pre-hydration condition. FIG. 6 shows a chitosan ureteral stent in hydrated condition. It has a pigtail on either end of the stent. These chitosan based ureteral stents generally have a stent length in the range of from 20 to about 26 cm, with an outer diameter in the range between about 2.0 and about 2.5 mm, and an internal diameter in the range of between about 1.0 and about 1.2 mm. The chitosan content of these chitosan stents is in the range of from about 70 to 85 weight percentage of the total stent weight, and the remaining component may be barium sulfate in the amount of from about 15 to about 30 weight percentage of the total stent weight. The pigtail strength of these chitosan based ureteral stents is generally in the range of between about 0.0400 and 0.550 N. The acetylation degree of these chitosan based ureteral stents is generally in the range of between about 10% and about 20%.

Example 3

Figure 7:
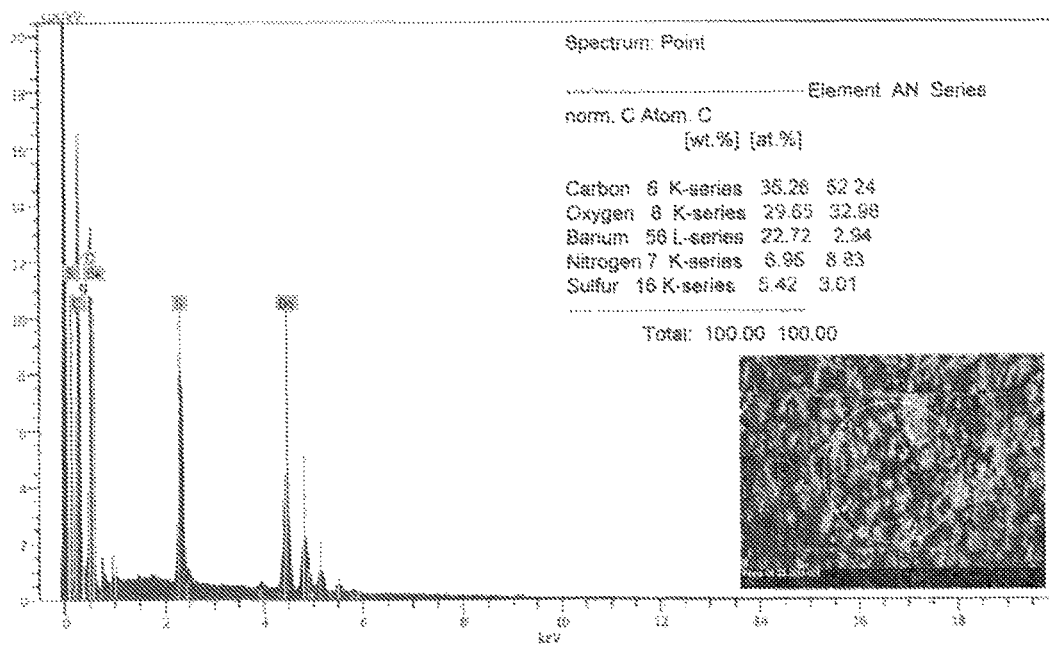
FIG. 7 shows the elemental analysis result using Bruker Quantax 70 Energy Dispersive Spectroscopy (EDS).

FIG. 7 shows the morphology and the result of the elemental analysis result for 6 Fr. hydrated ureteral chitosan stent. Morphology picture was obtained with Hitachi™ 3000 scanning electron microscope (SEM); and the element analysis was performed with Bruker Quantax 70 Energy Dispersive Spectroscopy (EDS).

Example 4

Figure 8:
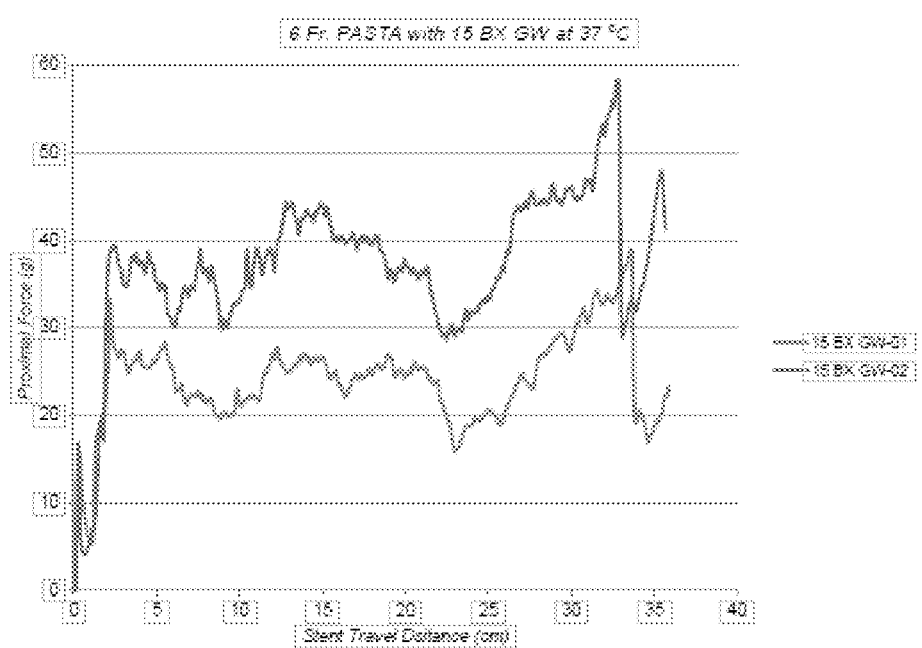
FIG. 8 shows the relationship between the proximal force and the inserting distance using an E-Z Glider® guidewire to deliver a chitosan based stent.

FIG. 8 shows the force that was used to push the chitosan stent through. The steady force shows that the guidewire under testing should be suitable for chitosan based stent. MSI Insertion Profile of 6 Fr. PASTA Stent with 15BX Easy Glide GW at 37° C. (III), Stent insertion force is measured with MSI IDTE 2000 system. Average stent insertion force is in range of 57.7±18.3 g. Maximum stent insertion force is in range of 74.3±22.1 g.

Example 5

FIG. 9 shows different guidewires used for chitosan based stents. It's quite clear that the hydrophilic E-Z Glider® guidewires are suitable for the delivery of the chitosan based stents. The E-Z Glider® guidewires are from Gyrus ACMI, Inc. These guidewires are either coated with Polyvinylpyrrolidone (PVP), or with and polyacrylic acid (PAA). The chitosan based chitosan stents have contact angles between 20 and 80, and the PVPs have contact angles between 60 and 60, and PAA have contact angles of between 30 and 63 degree.

In summary, all these test results indicated that the chitosan based stents could not be placed into proper position by PTFE coated guidewires. On the contrary, they can be delivered by the hydrophilic coated E-Z Glider® guidewires. Moreover, the tests also showed the extra 10 min hydration step for the chitosan based stents would improve their performance even though bench-top stent performance test results showed that the chitosan based stents can be safely used under pre-hydration condition up to three weeks.

INCORPORATION BY REFERENCE

The contents of all references, patents, pending patent applications and published patents, cited throughout this application are hereby expressly incorporated by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. A method of identifying a guidewire for the proper delivery of a biodegradable stent into a treatment site of a patient, the method comprising determining the surface hydrophilicity or surface hydrophobicity of a guidewire through measuring a contact angle of its surface; and determining the surface hydrophilicity or surface hydrophobicity of a biodegradable stent through measuring a contact angle of its surface, wherein the guidewire is proper for the delivery of the stent when the guidewire is a hydrogel coated guidewire having a contact angle of between about 20 and about 80 degrees and the stent is a chitosan based stent having a contact angle of between about 20 and about 80 degrees.

2. The method of claim 1, further comprising delivering the biodegradable stent into the treatment site of the patient using the properly identified guidewire.

3. The method of claim 1, wherein the biodegradable stent is a chitosan based ureteral stent.

4. The method of claim 1, wherein the hydrogel coated guidewire is a polyvinylpyrrolidone coated guidewire or a polyacrylic acid coated guidewire.

\* \* \* \* \*